US00PP16332P2

(12) United States Plant Patent
Hansen

(10) Patent No.: US PP16,332 P2
(45) Date of Patent: Mar. 14, 2006

(54) ***CAREX* PLANT NAMED 'TREASURE ISLAND'**

(50) Latin Name: *Carex ciliato-marginata*
Varietal Denomination: Treasure Island

(75) Inventor: Hans Andrew Hansen, Waseca, MN (US)

(73) Assignee: Shady Oaks Nursery, LLC, Waseca, MN (US); part interest ( * ) Notice: Subject to any disclaimer, the term of this patent is extended or adjusted under 35 U.S.C. 154(b) by 178 days.

(21) Appl. No.: 10/964,108

(22) Filed: Oct. 12, 2004

(51) Int. Cl.
*A01H 5/00* (2006.01)

(52) U.S. Cl. ..... Plt./373

(58) Field of Classification Search ..... Plt./373
See application file for complete search history.

*Primary Examiner*—Anne Marie Grunberg
(74) *Attorney, Agent, or Firm*—Penny J. Aguirre

(57) ABSTRACT

A new cultivar of *Carex ciliato-marginata,* 'Treasure Island' characterized by its variegated foliage with white margins and green centers, a spreading habit with suitable use as a groundcover and a vigorous growth rate.

2 Drawing Sheets

Botanical classification: *Carex ciliato-marginata.*
Varietal denomination: 'Treasure Island'.

BACKGROUND OF THE INVENTION

The present invention relates to a new and distinct cultivar of *Carex ciliato-marginata* and will be referred to hereafter by its cultivar name, 'Treasure Island'. 'Treasure Island' is a new cultivar of perennial ornamental grass grown for landscape use.

The inventor discovered the new cultivar, 'Treasure Island' in November of 2001 as a sport of *Carex ciliato-marginata* 'Island Brocade' (not patented) in a tissue culture lab in Waseca, Minn.

The new cultivar 'Treasure Island' was selected for the unique foliage variegation pattern comprised of leaves with white margins and green centers. The parent, 'Island Brocade', has variegated foliage with creamy yellow margins and green centers. 'Treasure Island' is also more vigorous in growth rate in comparison to 'Island Brocade'.

Asexual reproduction of the new cultivar was first accomplished by in vitro propagation of adventitious tissue in Waseca, Minn. in November of 2001 by the inventor. The characteristics of this cultivar have been determined to be stable and are reproduced true to type in successive generations.

SUMMARY OF THE INVENTION

The following traits have been repeatedly observed and represent the characteristics of the new cultivar. The new *Carex* has not been observed under all possible environmental conditions. The phenotype may vary somewhat with variations in temperature, day-length, light intensity, soil types, and water and fertility levels without, however, any variance in genotype. The general observations, and descriptions that follow describe plants that were grown outdoors in a test plot in Waseca, Minn. for a period of two years. These attributes in combination distinguish 'Treasure Island' from all other selections of *Carex* known to the inventors.

1. The foliage of 'Treasure Island' is variegated with leaves that exhibit a primary pattern of white margins and green centers, while the parent plant has creamy yellow margins. The variegation pattern is further characterized by the presence of thin white stripes the centers and the presence of thin green stripes in the margins.
2. The growth rate of 'Treasure Island' is about 3 times that of 'Island Brocade'. 'Treasure Island' has a greater growth rate in comparison to 'Island Brocade'. A 32-cell plug of 'Treasure Island' will fully develop in a 4 inch container in about 2 weeks while a 4 inch container of 'Island Brocade' requires 6 weeks.
3. 'Treasure Island' obtains a height of about 8 cm and a spread of about 20 cm in two growing seasons from a 72-cell plug when grown in the ground in Minnesota.
4. 'Treasure Island' has a spreading habit and is suitable for use as a groundcover.

BRIEF DESCRIPTION OF THE DRAWING

The accompanying colored photographs illustrate the overall appearance and distinct characteristics of the new *Carex.*

The photograph in FIG. 1 was taken in late summer and illustrates the overall habit and appearance of 'Treasure Island' in Waseca, Minn. as grown outdoors for two years after planting from a 72-cell plug.

Figure 1:
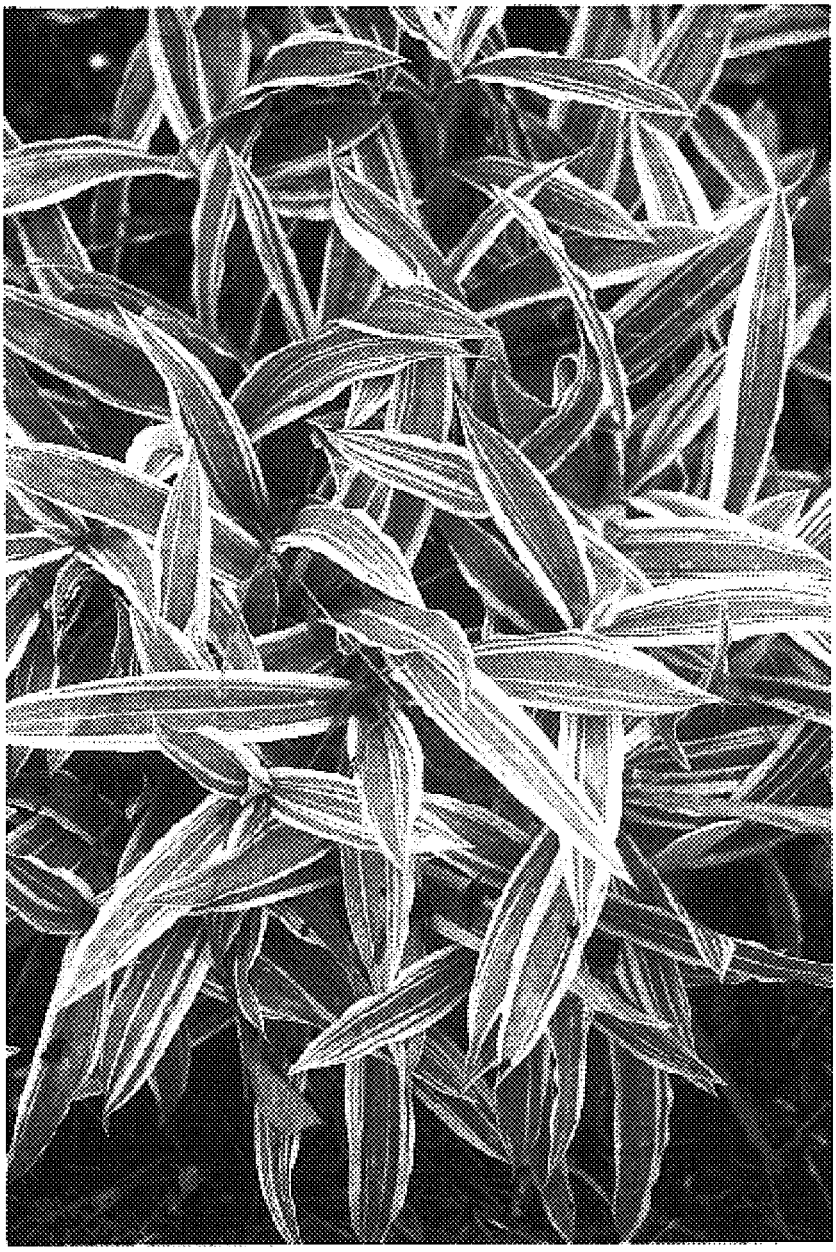
Figure 2:
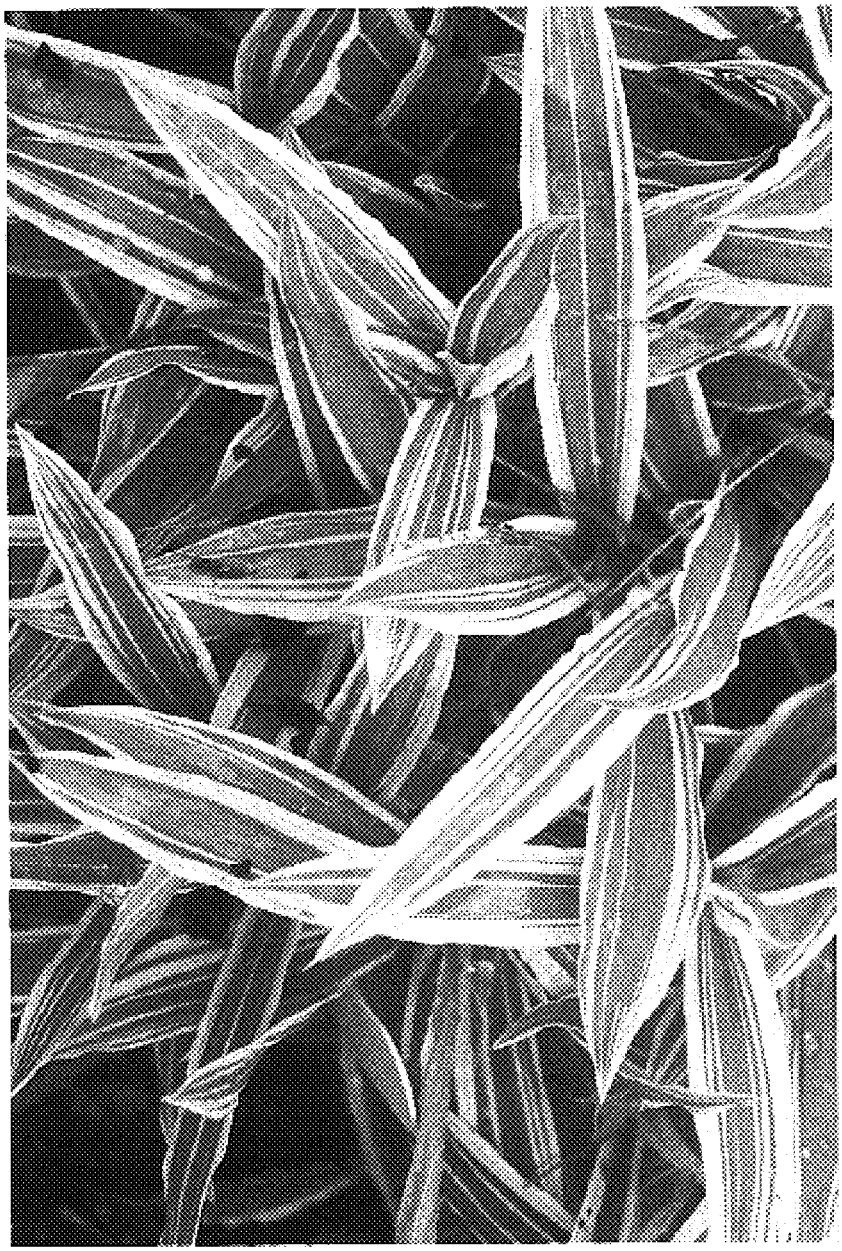

The photograph on FIG. 2 is a close-up view of the variegation pattern characteristic of the foliage of 'Treasure Island'. The colors in the photographs are as close as possible with the photographic and printing technology utilized and the color values cited in the detailed botanical description accurately describe the colors of the new *Carex.*

DETAILED BOTANICAL DESCRIPTION

The general observations and descriptions describe plants that were grown outdoors in Waseca, Minn. from a 72-cell plug for two growing seasons. The color determinations are in accordance with the 2001 R.H.S. Colour Chart of The Royal Horticultural Society, London, England, except where general color terms of ordinary dictionary significance are used.

Botanical classification: 'Treasure Island' is a cultivar of *Carex ciliato-marginata.*

Parentage: Sport of *Carex ciliato-marginata* 'Island Brocade', derived in tissue culture.

General description:

*Plant habit.*—Herbaceous, ornamental grass with a spreading habit, suitable for use as a groundcover.

*Height and spread.*—Reaches about 8 cm in height and spreads as a groundcover. A 32-cell plug grown in the ground in Minnesota obtained a spread of about 17 cm at the base and 20 cm to the edges of the foliage in two growing seasons.

*Cold hardiness.*—USDA Zones 4–8.

*Culture.*—Grows best in part shade in fertile, well-drained soils with adequate moisture.

*Diseases and pests.*—No unique aspects concerning susceptibility or resistance to diseases or pests that are known to affect *Carex* have been observed.

*Root description.*—Short, knotty rhizomes with wiry roots, about 1 cm in length, about 0.4 cm in width.

*Branching.*—Stemless, shoots arise from rhizomes.

Growth and propagation:

*Propagation.*—Tissue culture or rhizome division, basal stem cuttings.

*Time required for root development.*—A rooted tissue culture propagule will fully develop in a 32 cell plug in about 4 weeks when grown in the greenhouse at a average temperature of 68° F. under natural lighting in Minnesota.

*Growth rate.*—Vigorous, a 72-cell plug will finish in a 4 inch container in about 2 weeks when grown in a greenhouse at an average temperature of 68° F. under natural light in Minnesota in the spring.

Foliage description:

*Leaf shape.*—Lanceolate.

*Leaf division.*—Simple.

*Leaf base.*—Sheathed to rhizome.

*Leaf apex.*—Acute.

*Leaf aspect.*—Leaves initially emerge upright, then cascade downward with lower leaves nearly horizontal.

*Leaf venation.*—Parallel, the midrib is raised on the lower surface, not prominent or conspicuous, color matches leaf color.

*Leaf margins.*—Entire, slightly wavy on mature foliage.

*Leaf persistence.*—Dry to a brown color, 177B, but remain are persistent through winter.

*Leaf attachment.*—Sheathed.

*Leaf size.*—Up to about 1.8 cm in width and up to about 15 cm in length.

*Leaf number.*—5 to 8 leaves per shoot in mid September.

*Leaf arrangement.*—Equitant (overlapping), emerge from center, sheathed to base.

*Leaf surface.*—Glabrous on upper and lower surface.

*Leaf color and variegation pattern.*—Basic variegation pattern on emerging and mature foliage consists of medium green centers with white stripes and white margins, margins are 1 to 3 mm in width and stripe widths range from 0.5 mm to 1 mm, there are typically 1 to 3 vertical white stripes in the centers. Emerging leaf color; upper surface; centers 143A with margins and stripes 155B, lower surface: centers 144A with margins and stripes 155B. Mature leaf color; upper surface: centers range from 137 A or 137B to a color between 137A and 138A with margins and stripes 158A to 158B, lower surface: centers 138A to 138B with margins and stripes 158A to 158B. Base of leaves colored red (50C) but not generally visible.

Flower and seed description: Flowering has not been observed.

I claim:

1. A new and distinct cultivar of *Carex* plant named 'Treasure Island' as herein illustrated and described.

* * * * *